United States Patent [19]

Adiutori

[11] Patent Number: 4,916,715
[45] Date of Patent: Apr. 10, 1990

[54] METHOD AND APPARATUS FOR MEASURING THE DISTRIBUTION OF HEAT FLUX AND HEAT TRANSFER COEFFICIENTS ON THE SURFACE OF A COOLED COMPONENT USED IN A HIGH TEMPERATURE ENVIRONMENT

[75] Inventor: Eugene F. Adiutori, Westchester, Ohio

[73] Assignee: General Electric Company, Cincinnati, Ohio

[21] Appl. No.: 180,926

[22] Filed: Apr. 13, 1988

[51] Int. Cl.[4] ...................... G01K 17/00; G01N 25/20
[52] U.S. Cl. .......................................... 374/29; 374/1; 374/43; 374/134
[58] Field of Search ...................... 374/29, 137, 43, 44, 374/134, 30; 219/201

[56] References Cited

U.S. PATENT DOCUMENTS

| | | | |
|---|---|---|---|
| 1,528,383 | 3/1925 | Schmidt | 374/30 |
| 2,585,934 | 2/1952 | Haswell | 73/359 |
| 3,095,743 | 7/1963 | Teasel et al. | 374/134 X |
| 3,123,996 | 3/1964 | Musial | 73/15 |
| 3,221,554 | 12/1965 | Kuether | 374/30 X |
| 3,354,720 | 11/1967 | Hager, Jr. | 374/132 |
| 3,592,061 | 7/1971 | Schwedland et al. | 73/343 |
| 3,623,368 | 11/1971 | Decker | 73/343 |
| 3,672,204 | 6/1972 | Green | 73/15 |
| 4,024,751 | 5/1977 | Potrzebowski | 374/43 |
| 4,058,975 | 11/1977 | Gilbert et al. | 473/145 X |
| 4,309,991 | 1/1982 | Rolinski et al. | 374/1 X |
| 4,553,852 | 11/1985 | Derderian et al. | 374/30 X |
| 4,568,198 | 2/1986 | Szabo et al. | 374/29 X |
| 4,595,298 | 6/1986 | Frederick | 374/144 |
| 4,644,162 | 2/1987 | Bantel et al. | 250/340 |
| 4,812,050 | 3/1989 | Epstein | 374/29 |

OTHER PUBLICATIONS

"Thick Film Thermocouple Gages . . . For Heat Flux Measurements", by K. E. Starner et al., 24th ISA Conference, Oct. 27-30, 1969, 7 pp. of #581.

Primary Examiner—Daniel M. Yasich
Attorney, Agent, or Firm—Jerome C. Squillaro; Steven J. Rosen

[57] ABSTRACT

Heat flux distribution and heat transfer coefficient distribution over a surface of a component used in a high temperature environment are determined by supplying coolant of predetermined characteristics to the component and measuring a temperature distribution over a predetermined surface. The heat flux at each temperature measurement point on the surface of the component is determined from heat flux calibration data obtained before the component is placed in service and while it is being operated at in-service cooling conditions. The heat transfer coefficient at various locations on the surface of the component is determined from the heat flux indicated by the heat flux calibration data, the temperature of the surface, and the temperature of the environment in which the component is situated.

35 Claims, 2 Drawing Sheets

METHOD AND APPARATUS FOR MEASURING THE DISTRIBUTION OF HEAT FLUX AND HEAT TRANSFER COEFFICIENTS ON THE SURFACE OF A COOLED COMPONENT USED IN A HIGH TEMPERATURE ENVIRONMENT

FIELD OF THE INVENTION

This invention relates to the design of cooled components used in machinery. More particularly, this invention relates to a method and apparatus for measuring the distribution of heat flux and heat transfer coefficients on the surface of cooled components, such as those found in gas turbine engines and other machinery employing cooled components in a high temperature environment.

CROSS REFERENCES TO RELATED PATENT APPLICATIONS

Application Ser. No. 180,819, filed Apr. 13, 1988, of Eugene F. Adiutori, entitled "APPARATUS AND METHOD FOR MEASURING THE THERMAL PERFORMANCE OF A HEATED OR COOLED COMPONENT."

Application Ser. No. 181,128, filed Apr. 13, 1988, of Eugene F. Adiutori and James E. Cahill, entitled "APPARATUS AND METHOD FOR DETERMINING HEAT TRANSFER COEFFICIENT BASED ON TESTING ACTUAL HARDWARE RATHER THAN SIMPLISTIC SCALE MODELS OF HARDWARE."

BACKGROUND OF THE INVENTION

It is well known to provide mechanical components in machinery, such as gas turbine engines, with cooling systems in order to permit operation of the machinery at higher temperatures than would be possible without such cooling systems. The higher operating temperatures permitted by such cooling systems result in increased performance and efficiency of the machinery.

To design an optimum cooling system for components which will operate in a high temperature environment, it is necessary to determine the heat flux distribution on a surface of the component which is exposed to high temperature. One known method of determining the heat flux distribution is to take actual measurements in an operating system using commercially available heat flux gauges placed on the surface of the component. Examples of such gauges are those obtainable from RdF Corporation of Hudson, N.H. However, these gauges cannot be used in applications where the temperature to which the gauges are exposed exceeds their maximum permissible operating temperature, typically about 500 degrees Fahrenheit. This maximum permissible temperature is too low to take meaningful measurements on a component used in a high temperature environment such as a gas turbine engine in which temperatures may exceed 2000 degrees Fahrenheit. Also, the commercially available film heat flux gauges have dimensions on the order of 0.25 to 0.50 inches making them too large for many applications. In addition, these gauges have considerable thermal resistance which influences heat flux magnitude and distribution and thus may produce serious measurement errors. The heat flux gauges typically have thermal resistances of about 0.003 to 0.010 degrees Fahrenheit/BTU/hr.ft.$^2$ which can cause considerable error when measuring equipment exposed to large amounts of heat flux.

There are commercially available heat flux gauges which can withstand high temperature, for example, circular foil heat flux gauges sold by Thermogage, Inc. of Frostburg, Md. They are about 0.5 to 1.0 inches in diameter, too large to be used on small components.

A second known method of determining heat flux distribution involves predicting heat flux distribution on the surface of a component based solely on analysis. The heat transfer coefficient ("h") is calculated analytically and the heat flux ("q/A") distribution as a function of "x" and "y" coordinate is computed using the following equation:

$$(q/A)_{x,y} = h_{x,y}(T_{mainstream} - T_{surface,x,y}), \qquad (1)$$

where $T_{mainstream}$ is the temperature of the environment in which the component is being operated, for example, the temperature of a hot fluid flowing over the surface of the component. $T_{surface}$ is the temperature of the surface for which the heat flux distribution is being determined. However, since it is not possible to accurately predict the heat transfer coefficient "h" except for very simple geometries, this method of determining heat flux distribution is not accurate or reliable for many components having complicated geometries such as those found in modern aircraft engines.

A third known method of determining heat flux distribution involves predicting the heat flux distribution based on an extrapolation of laboratory test measurements taken on a model of the component or taken on the component itself. When using a model, the model is commonly situated in a cool environment with electrical heaters attached to the surface of the model, for example, a series of wire resistance heaters, such as Calrod heaters, situated in grooves machined into the surface of the model. The power supplied to the heaters, $T_{mainstream}$, and $T_{surface}$ are measured. Heat flux is calculated in light of measured heater power and local values of heat transfer coefficient "h" obtained from equation 1. The local values of heat transfer coefficient "h" obtained from the model are extrapolated to equipment design conditions to obtain "h" values for the actual component. Heat flux distribution for the actual component is then calculated from the relationship of equation 1.

However, the accuracy of the heat transfer coefficient distribution obtained using this method is compromised due to the fact that the surface of the model is hotter than the environment. The temperature difference across the boundary layer between the component and the environment is therefore in a direction opposite that for a cooled component in a hotter environment. Since the measured heat transfer coefficient depends on the direction of the temperature difference across the boundary layer, the accuracy of the heat flux distribution calculated with these measured heat transfer coefficients is adversely affected and may not be accurate for actual components operating in an actual apparatus. This method also suffers from the fact that the heaters must be isolated from each other and operated at the same temperature to minimize cross conduction of heat. Specifically, each heater zone must have dimensions of at least 0.25 inches which is too large for testing small components.

Laboratory test measurements taken from an actual component may also be extrapolated to real life operating conditions. In this situation, the component is operated in a high temperature environment with heat flux gauges mounted on its surface. Heat flux values are read from the gauges and $T_{surface}$ and $T_{mainstream}$ are measured. Heat transfer coefficient values "h" are calculated using equation 1. The "h" values determined under laboratory conditions are then extrapolated to real life conditions. However, since heat flux gauges are used, the problems inherent with the use of such gauges are present in this method, as they have been in the method described above which also uses such gauges.

In light of the difficulties present in known methods of determining heat flux distribution and heat transfer coefficient distribution on surfaces of cooled components, a long standing and unfulfilled need has existed for a different method of measuring these parameters which avoids those difficulties.

SUMMARY OF THE INVENTION

This invention solves the problems of the prior art and satisfies the long standing need identified above. One example of the invention involves determining the heat flux and heat transfer coefficient distribution on the surface of a cooled component by attaching a plurality of temperature measuring devices to a predetermined surface of the component, attaching a heater to a preselected surface of the component, applying a cooling fluid flow having predetermined characteristics to the component, applying a plurality of amounts of power to the heater, measuring the heater power level, the coolant temperature, and the temperature at the surface of the component, and deriving a heat flux calibration data for each temperature measuring device from the heater power, the coolant temperature, and the output of the temperature measuring device. The heat flux calibration data measured in this manner may be used to derive heat flux and heat transfer coefficient distributions for the cooled component in the environment in which it is used.

DETAILED DESCRIPTION

An example of the invention is given here which will illustrate how it satisfies the long standing needs of the prior art. This example of the invention involves attaching a plurality of thermocouples to a surface of a cooled component and calibrating the thermocouples in such a way that the temperature read from the thermocouples and the temperature of coolant supplied to the component define the heat flux at the location of each thermocouple. After calibration, the component is placed in service and cooled in the same manner as it was cooled when the calibration was performed. Calibration curves produced in connection with the calibration operation are used to determine the heat flux at the surface of the component from the outputs of the thermocouples. If desired, the heat transfer coefficient at the location of each thermocouple is determined by dividing the heat flux measured by each thermocouple by the difference between the mainstream temperature and the temperature measured by each thermocouple.

The calibration of the thermocouples involves applying heat to a predetermined area on the surface of the component. This may be accomplished by attaching a thin resistive, foil heater to the predetermined area of the component. Instead of a single heater, a plurality of heaters may be used which are able together to apply heat to the predetermined surface. The calibration also involves applying coolant of predetermined characteristics to the component, applying a plurality of known amounts of electrical power to the heater or heaters, and measuring the heater area, the heater power levels, the characteristics of the coolant, such as flow rate, pressure, and temperature, and the temperatures at the surface of the component. The calibration is completed by generating calibration data of surface heat flux versus temperature (or temperature difference between the thermocouple and coolant) for each thermocouple.

Figure 1:
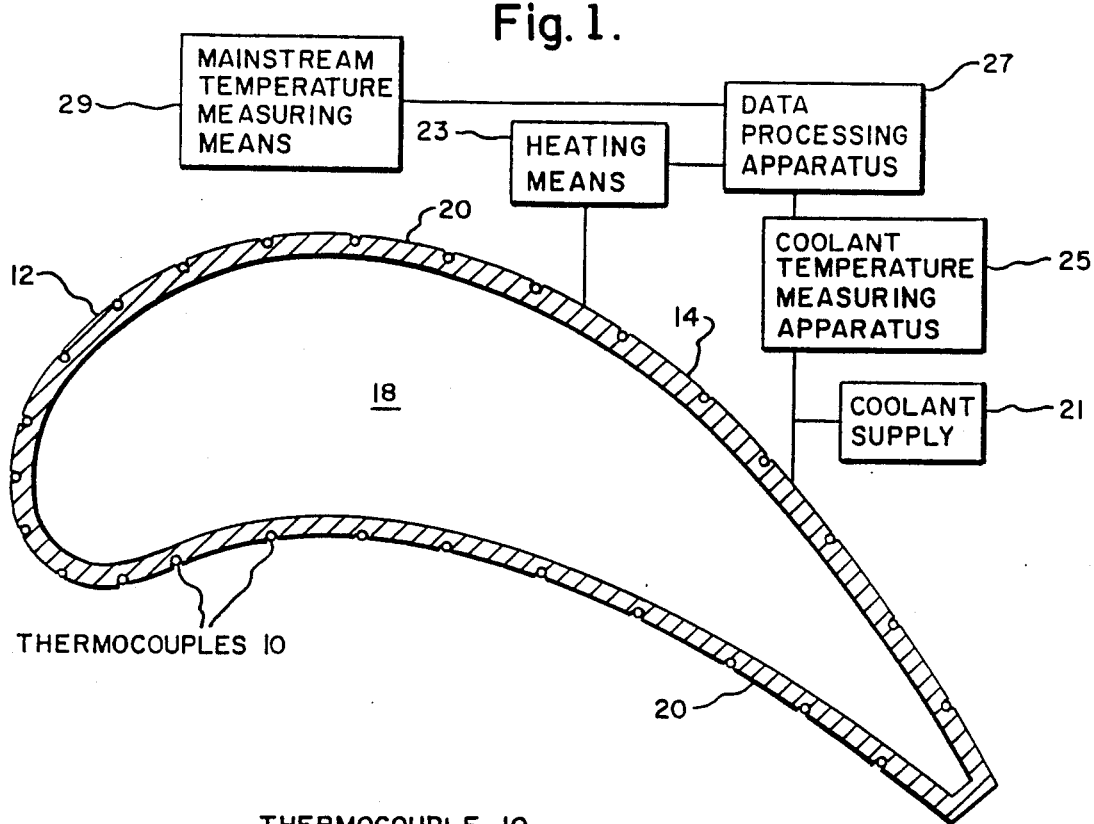
FIG. 1 represents a partly schematic representation including a cross section of a hollow turbine blade having thermocouples attached to the outer surface of the blade in accordance with one example of this invention.

A detailed description of the example of the invention summarized above is given here. As a first step in carrying out this example of the invention, a heat flux calibration described above is performed on a cooled component. Small diameter type K thermocouples, such as known thermocouples having a diameter of about 0.010 inches, which are capped, grounded, and MgO insulated, and have stainless steel or Inconel sheaths, are installed in shallow grooves machined at a plurality of locations on the outer surface of a component having at least one cooling passage. FIG. 1 shows an example of this kind of a component in the form of a hollow turbine blade 12 having thermocouples installed in grooves machined into the outer surface of the turbine blade 12. Two of those thermocouples are indicated in FIG. 1 with a reference numeral 10.

The turbine blade 12 is normally exposed to high temperatures which may damage or destroy the blade. Those temperatures may exceed 2000 degrees Fahrenheit. To minimize the risk of damage caused by excessive temperatures, the turbine blade 12 has a cooling passage 18 through which cooling fluid is directed to maintain the temperature of the blade at a safe level. Normally, the cooling fluid for components, such as the turbine blade of FIG. 1, is water and the invention works best for components that are water cooled, although it is not required that the components tested in accordance with the invention be water cooled to obtain beneficial results. Specifically, since the fluid used in the steps described below should be the same as that used to cool the component in actual operation, the invention works the best when water is used in the steps described below relating to supplying coolant of predetermined characteristics to the blade during testing.

Although the invention of this application may be carried out with a wide variety of cooled components, it is preferred that it be carried out with hollow components having uniform, thin walls because the results are easier to interpret. This is because there is little heat flow parallel to the surfaces of such structures and, therefore, the results can be interpreted as being based on one dimensional heat flow.

Figure 2:
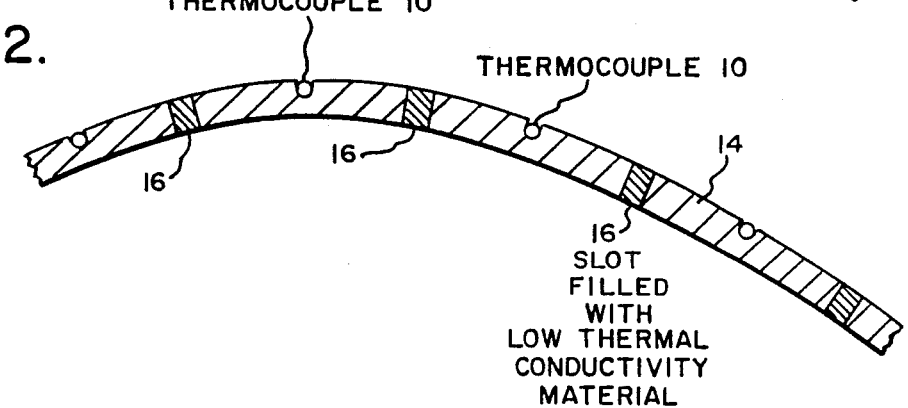
FIG. 2 represents part of a cross section of a turbine blade having slots filled with low thermal conductivity material between thermocouples attached to the outer surface of the blade in accordance with a second example of this invention.

Accordingly, not only is the turbine blade 12 in FIG. 1 hollow, but also the wall 14 of the blade is uniform and thin to discourage transverse heat flow to ensure the accuracy of results based on one dimensional analysis. In components having areas analogous to wall 14, where there is a possibility of an extreme gradient in heat flux resulting in heat flow parallel to the surfaces of the blade, the wall may be provided with slots 16, as shown in FIG. 2, which are filled with a low thermal conductivity material, such as a plastic material or asbestos, which would discourage such heat flow parallel to the surfaces of the blade.

After the thermocouples have been attached to the surface of the blade, a thin resistive, foil heater 20, such as a Minco HK131118742 heater, having a known area is then attached to the exterior surface of the component so that it covers the thermocouples and a large portion of the outer surface of the component. The outer surface of the blade is then insulated to ensure that most of the heat flows into the blade and its coolant and not into the blade's surroundings. A coolant flow having predetermined characteristics is then directed through the cooling passage 18. As stated above, the invention works best when the coolant is water. Any generally known source 21 of coolant may be used to supply coolant as long as the source is capable of supplying coolant at a known temperature and pressure or at a known temperature and flow rate.

Several predetermined levels of electrical power are then applied to the film heater by means 23 for applying a plurality of predetermined amounts of heating to the blade 12 by way of the heater 20. For each level of electrical power applied to the heater, the coolant temperature as measured by any well known apparatus 25 for measuring such coolant temperatures is taken, for example, by a thermocouple situated at the inlet to the passage 18. The surface temperatures as measured by the thermocouples are also taken while heat flux and coolant are being applied to the component. The heat flux at each heater power is computed from the electrical power input to the heater and the known surface area of the heater.

Figure 3:
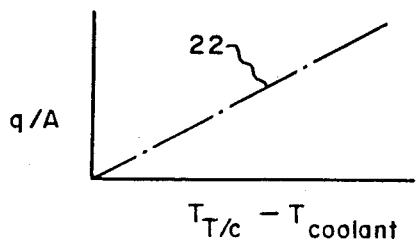
FIG. 3 is a schematic representation of a plot of heat flux as a function of the difference between the temperature of a thermocouple attached to the exterior surface of a hollow turbine blade and the temperature of a coolant flowing through the interior of the turbine blade.

The results of these measurements and computation is used to produce a calibration data in the form of a curve. The results may be plotted on a graph such as the one shown in FIG. 3 which shows heat flux as a function of the difference between the temperature measured by a surface thermocouple and the temperature of the coolant. The data may also be input to a data processing apparatus 27 which is capable of storing the data, computing the heat flux, and deriving an equation defining the calibration curve. In this instance, the heat flux for each surface thermocouple will generally be a linear function of the difference between the thermocouple and coolant temperatures. In other words, if the function is plotted manually, it generally will be essentially a straight line on linear paper, as indicated by an illustration of such a line 22 in FIG. 3.

After the heat flux calibration is performed, the heater is then removed from the turbine blade. The thermocouples are left attached to the surface of the blade. The curves resulting from the heat flux calibration are used along with the outputs of the thermocouples to determine heat flux at each thermocouple when the turbine blade is subsequently tested in an actual system, or in a laboratory experiment, while the blade is being supplied with coolant of the same characteristics as that used in the calibration. More specifically, at a number of test points, the heat flux at each thermocouple may be determined by simply measuring the temperature difference between the coolant and the thermocouple and finding the heat flux at the thermocouple from the calibration curve for that thermocouple. To determine the heat transfer coefficient at each thermocouple, "h" in equation 1 above, $T_{mainstream}$ is measured by means 29 for measuring mainstream temperature and equation 1 is solved for "h" using the heat flux obtained from the calibration curve. The computation of the heat flux and heat transfer coefficient distributions may be made by an electronic data processing apparatus such as a programmed digital computer which has been provided with electrical signals representing the measured and calculated quantities described above. The data processing apparatus may be the same data processing apparatus referred to in connection with the description of the calibration operation above.

Figure 4:
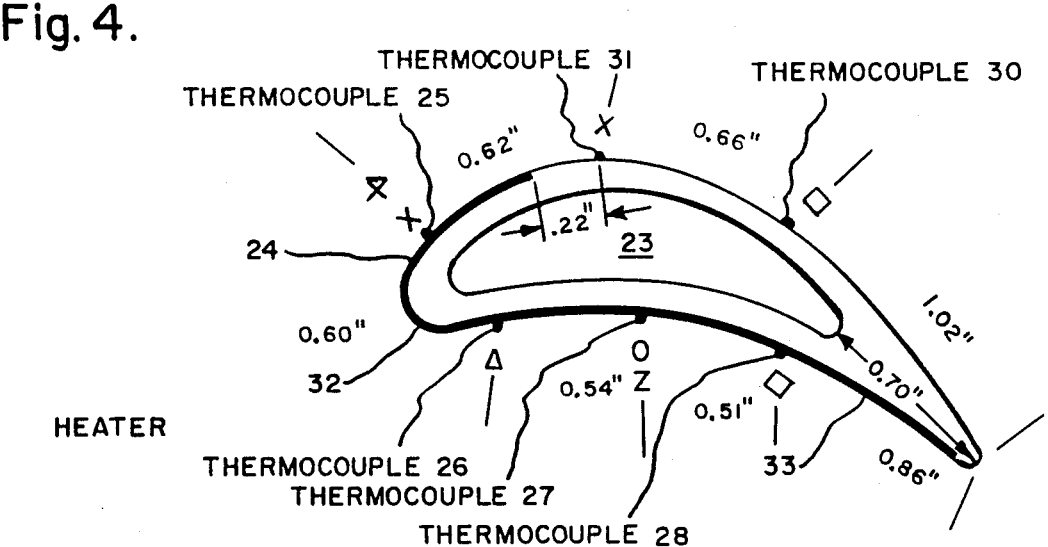
FIG. 4 is a cross section of a turbine blade instrumented in accordance with an additional embodiment of the invention.

FIG. 4 is a cross section of another turbine blade 24 instrumented in accordance with the invention of this application. The turbine blade 24 has a number of thermocouples attached to the exterior surface of the blade. The thermocouples at the location the blade is sectioned are indicated in FIG. 4 by reference numerals 25-28, 30, and 31. A thin resistive, foil heater indicated by a heavy black line 32 is attached to a part of the exterior surface of the blade so as to cover thermocouples 25-28. The covered thermocouples 25-28 will be used to ascertain heat flux and heat transfer coefficient distributions. Thermocouples 30 and 31 are left uncovered. The output of thermocouples 30 and 31 may be used to confirm that heat flow from the outside of the blade to the inside of the blade is one dimensional as described in more detail below. A film thermocouple 33 may be attached to the outside surface of the heater to monitor the temperature of the heater, if such data is desired. There may be a plurality of such film thermocouples attached to the heater if it is desired to measure the heater temperature at a number of locations. In addition to thermocouples 25-28, 30, and 31, a temperature measuring device not shown in FIG. 4 is provided to measure the temperature of cooling fluid passing through the hollow interior 23 of the blade. This temperature measuring device may be another thermocouple situated so that it is exposed to the cooling fluid as it enters or leaves the blade.

Figure 5:
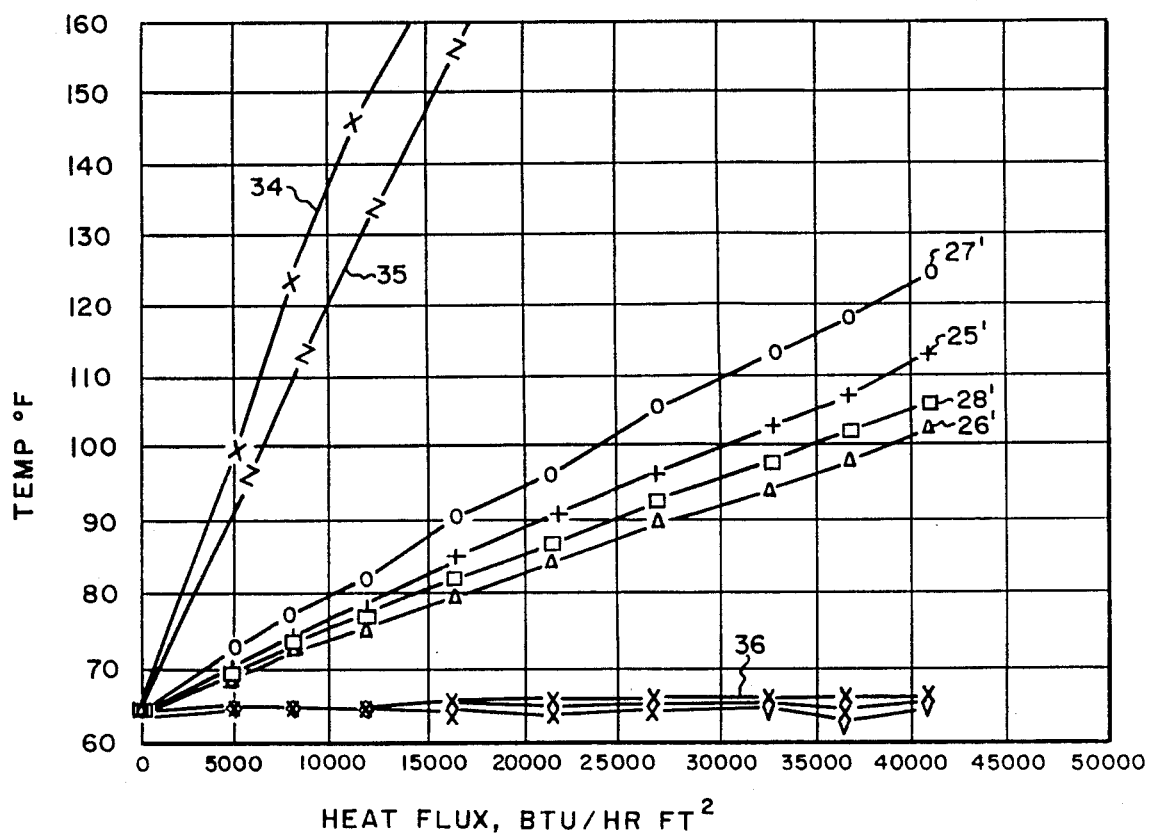
FIG. 5 is a graph showing the heat flux versus temperature relationships for the thermocouples located on, or in the vicinity of, the hollow turbine blade shown in cross section in FIG. 4.

FIG. 5 is a graph illustrating data taken from the instrumented turbine blade of FIG. 4 relating heat flux to thermocouple temperature at a number of heater powers. The graph shows a series of data points each having two coordinates. One of the coordinates is the heat flux at each level of heater power. As in the previous example of FIG. 1, the heat flux is derived from the known amount of heater power being applied to the turbine blade and the known area of the heater. The other coordinate of the data points in FIG. 5 is the temperature at a particular thermocouple, which is derived from the output of that thermocouple at each level of heat flux. A smooth curve is drawn through each set of heat flux and temperature coordinates for each of the thermocouples. Each curve for the thermocouples covered by the heater is keyed to a corresponding thermocouple in FIG. 4 by a primed reference numeral in FIG. 5. Curves 34 and 35 relate heat flux to temperature for thermocouples used to measure heater temperature. Since the curves for the coolant temperature measuring thermocouple and thermocouples 30 and 31 are virtually the same on the scale of FIG. 5, they have been given one reference numeral, 36. These three curves 36 relate heat flux to temperature for the thermocouple which measures the temperature of the coolant and for the thermocouples which are not covered by the heater, specifically, thermocouples 30 and 31 in FIG. 4.

As shown in FIG. 5, the curves for the coolant temperature measuring thermocouple and thermocouples 30 and 31 are nearly the same. They are substantially horizontal indicating that the temperature in the vicinity of the thermocouples does not change with increasing heat flux. This is not the case with thermocouples 25-28, however. The curves for thermocouples 25-28 indicate that the temperature in the vicinity of the thermocouples rises with increasing heat flux. Also evident from FIG. 5 is the fact that the heat transfer through the blade is essentially one dimensional, that is, heat flow is normal to the exterior surface of the blade. This is established by the difference between the curves for thermocouples 25 and 31 which are closest to the edge of the heater.

The curves for the thermocouples under the heater and for the thermocouple which measures the coolant temperature are useful in deriving the heat flux and heat transfer coefficient distributions for the blade in the vicinity of each surface thermocouple, as in the case of the arrangement of FIG. 1. Specifically, a line similar to line 22 in FIG. 3 may be derived for each thermocouple 25-28 from its respective curve 25'-28' and from the curve for the thermocouple which measures the coolant temperature. This is accomplished by subtracting the temperature coordinate of each coolant temperature data point from the corresponding temperature coordinate of the data points for each of thermocouples 25-28 at each heat flux coordinate. As before, the lines resulting from this may be used to determine heat flux and heat transfer coefficient distributions for a turbine blade 24 operating in a real life environment, or in a simulation such as a cascade.

I claim:

1. A method for determining heat flux on a surface of a component, comprising the steps of:
    attaching one or more temperature measuring devices to a predetermined surface of a component for measuring the temperature of the predetermined surface at the location of each temperature measuring device;
    attaching a heater to a preselected surface of the component;
    applying coolant having predetermined characteristics to the component;
    applying a plurality of predetermined amounts of heat to the heater while the coolant having predetermined characteristics is being applied to the component;
    measuring the temperature of the coolant and the temperature of the predetermined surface of the component for each predetermined amount of heat; and
    deriving heat flux calibration data for each temperature measuring device from the amount of heat applied to the surface, the temperature of the coolant, and the temperature of the predetermined surface to calibrate each said temperature measuring device so that temperature indicated by each said temperature measuring device and temperature of coolant applied to said component define heat flux at the location of said temperature measuring device.

2. The method of claim 1, in which the step of applying cooling fluid to the component comprises the step of applying cooling fluid to one or more passages in the component and the step of attaching a heater to a preselected surface of the component comprises the step of attaching the heater to an exterior surface of the component.

3. The method of claim 1, in which the coolant applying step comprises the step of applying coolant having a predetermined flow rate and temperature to the component.

4. The method of claim 1 in which the coolant applying step comprises the step of applying coolant having a predetermined pressure and temperature to the component.

5. The method of claim 1, in which the amount of heat applied to the surface is derived from the electrical power input to the heater and the area of the heater.

6. The method of claim 1, in which the step of attaching one or more temperature measuring devices to a predetermined surface of the component comprises the step of attaching one or more thermocouples to the predetermined surface of the component.

7. The method of claim 1, in which the step of attaching a heater to a predetermined surface of the component comprises the step of attaching a resistive, foil heater to the preselected surface of the component.

8. The method of claim 1, in which the component is a turbine engine component.

9. The method of claim 1, in which the component is a turbine blade.

10. The method of claim 1, in which the deriving step comprises the step of:
    deriving data defining a heat flux calibration curve for each temperature measuring device by determining values related to the predetermined amounts of heat applied to the component as a function of the difference in temperature between the surface and the coolant.

11. The method of claim 10, further comprising the steps of:
    removing the heater from the surface of the component;
    applying coolant of predetermined characteristics to the component;
    measuring the temperature of the surface at each temperature measuring device; and
    determining the heat flux at each temperature measuring device from the heat flux calibration curve and the temperature at each temperature measuring device after the heater has been removed.

12. The method of claim 11, in which the step of applying coolant of predetermined characteristics to the component comprises the step of applying coolant of the characteristics applied to the component with the heater attached to the component.

13. The method of claim 11, further comprising the steps of:
    measuring the mainstream temperature; and
    determining the heat transfer coefficient at each temperature measuring device from the heat flux at each temperature measuring device, the mainstream temperature, and the temperature measured by each temperature measuring device.

14. The method of claim 13, in which the determining step comprises the step of dividing the heat flux at each temperature measuring device by the difference between the mainstream temperature and the temperature at each temperature measuring device.

15. The method of claim 1, further comprising the steps of:
  removing the heater from the surface of the component;
  applying coolant of predetermined characteristics to the component;
  measuring the temperature of the surface at each temperature measuring device; and
  determining the heat flux at each temperature measuring device from the heat flux calibration data and the temperature at each temperature measuring device after removal of the heater.

16. The method of claim, 15, in which the step of applying coolant of predetermined characteristics to the component comprises the step of applying coolant of the characteristics applied to the component with the heater attached to the component.

17. The method of claim 15, further comprising the steps of:
  measuring the mainstream temperature; and
  determining the heat transfer coefficient at each temperature measuring device from the heat flux at each temperature measuring device, the mainstream temperature, and the temperature measured by each temperature measuring device.

18. The method of claim 17, in which the determining step comprises the step of dividing the heat flux at each temperature measuring device by the difference between the mainstream temperature and the temperature at each temperature measuring device.

19. An apparatus for determine heat flux on a surface of a component, comprising:
  one or more temperature measuring devices attached to a predetermined surface of the component for measuring the temperature of the predetermined surface at the location of each temperature measuring device;
  a heater attached to a preselected surface of the component;
  a means for supplying coolant of predetermined characteristics to the component;
  a means for measuring the temperature of the coolant supplied to the component;
  a means for applying a plurality of predetermined amounts of heating to the component by way of the heater;
  a means for recording the temperature of the coolant and the temperature of the surface of the component at the location of each temperature measuring device for each predetermined amount of heating; and
  a means for deriving heat flux calibration data for each temperature measuring device from the amount of heating applied to the surface, the temperature of the coolant, and the temperature of the surface to calibrate each said temperature measuring device so that temperature indicated by each said temperature measuring device and temperature of coolant applied to said component define heat flux at the location of said temperature measuring device.

20. The apparatus of claim 19, in which the deriving means comprises:
  a means for deriving data defining a heat flux calibration curve for each temperature measuring device by determining values related to the predetermined amounts of heating applied to the component as a function of the difference in temperature between the surface and the coolant.

21. The apparatus of claim 19, in which the coolant supplying means comprises a means for supplying coolant to the component having a predetermined flow rate and temperature.

22. The apparatus of claim 19, in which the coolant supplying means comprises a means for supplying coolant to the component having a predetermined pressure and temperature.

23. The apparatus of claim 19, in which the temperature measuring devices are one or more thermocouples.

24. The apparatus of claim 19, in which the heater is a resistive, foil heater.

25. The apparatus of claim 19, further comprising:
  a means for deriving the heat flux at one or more of the temperature measuring devices from the heat flux calibration data and the temperature measured by the temperature measuring means.

26. The apparatus of claim 25, further comprising:
  a means for deriving the heat transfer coefficient at one or more of the temperature measuring devices from the derived heat flux.

27. The apparatus of claim 26, in which the heat transfer coefficient deriving means comprises a means for measuring a mainstream temperature.

28. The apparatus of claim 27, in which the deriving means derives the heat transfer coefficient at the one or more temperature measuring devices from the derived heat flux, the measured mainstream temperature, and the temperature measured by the one or more temperature measuring devices.

29. An apparatus for determining the heat flux at one or more locations on a surface of a component in a high temperature environment, comprising:
  a means for applying coolant of predetermined characteristics to the component;
  a means for measuring the temperature at one or more locations on a predetermined surface of the component when it is operated in a high temperature environment; and
  means for determining the heat flux at the one or more locations on the component from derived heat flux calibration data related to said predetermined characteristics of said coolant and the output of the temperature measuring means.

30. An apparatus for determining the heat transfer coefficient for one or more locations on a surface of a component in a high temperature environment, comprising:
  a means for applying coolant of predetermined characteristics to the component;
  a means for measuring the temperature at one or more locations on a predetermined surface of the component when it is operated in a high temperature environment; and
  a means for determining the heat transfer coefficient for the one or more locations from derived heat flux calibration data related to said predetermined characteristics of said coolants and the output of the temperature measuring means.

31. A method for determining the heat flux at one or more locations on a surface of a component in a high temperature environment, comprising:

applying coolant of predetermined characteristics to the component;

measuring the temperature at one or more locations on a predetermined surface of the component when it is operated in a high temperature environment; and determining the heat flux at the one or more locations on the component from derived heat flux calibration data related to said predetermined characteristics of said coolant and the results of the temperature measurement step.

32. A method for determining the heat transfer coefficient at one or more locations on a surface of a component in a high temperature environment, comprising:

applying coolant of predetermined characteristics to the component;

measuring the temperature at one or more locations on a predetermined surface of the component when it is operated in a high temperature environment; and determining the heat transfer coefficient for the one or more locations from derived heat flux calibration data related to said predetermined characteristics of said coolant and the results of the temperature measurement step.

33. A method for determining heat flux on a predetermined surface of a component, comprising the steps of:

applying coolant having predetermined characteristics to a preselected surface of the component;

applying a plurality of predetermined amounts of heat to the predetermined surface of the component while coolant having the predetermined characteristics is being applied to the component;

measuring the temperature of the coolant and the temperature of the predetermined surface of the component for each predetermined amount of heat; and deriving heat flux calibration date from the predetermined amount of heat being applied to the component, the measured temperature of the coolant, and the measured temperature of the predetermined surface so that temperature measured from the predetermined surface and said coolant define heat flux at the predetermined surface.

34. The method of claim 33, further comprising the step of:

deriving the heat flux for the predetermined surface of the component from the heat flux calibration data.

35. The method of claim 33, further comprising the step of:

deriving a heat transfer coefficient for the predetermined surface of the component from the heat flux calibration data.

* * * * *